US009521954B2

(12) United States Patent
Xu et al.

(10) Patent No.: US 9,521,954 B2
(45) Date of Patent: Dec. 20, 2016

(54) VIDEO ACQUISITION SYSTEM FOR MONITORING A SUBJECT FOR A DESIRED PHYSIOLOGICAL FUNCTION

(71) Applicant: Xerox Corporation, Norwalk, CT (US)

(72) Inventors: Beilei Xu, Penfield, NY (US); Lalit Keshav Mestha, Fairport, NY (US); Survi Kyal, Rochester, NY (US); Himanshu J. Madhu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 426 days.

(21) Appl. No.: 13/921,939

(22) Filed: Jun. 19, 2013

(65) Prior Publication Data

US 2014/0378842 A1    Dec. 25, 2014

(51) Int. Cl.
*A61B 5/00*     (2006.01)
*A61B 5/0205*   (2006.01)

(52) U.S. Cl.
CPC .......... *A61B 5/0077* (2013.01); *A61B 5/0205* (2013.01); *A61B 5/7278* (2013.01); *A61B 5/7221* (2013.01); *A61B 2562/04* (2013.01); *A61B 2576/00* (2013.01)

(58) Field of Classification Search
CPC .......... A61B 2562/04; A61B 2576/00; A61B 5/0077; A61B 5/0205; A61B 5/7221; A61B 5/7278
See application file for complete search history.

(56) References Cited

PUBLICATIONS

Liu et al., "Method and Systems for Vascular Pattern Localization Using Temporal Features", U.S. Appl. No. 13/710,794.
Mestha et al., "Removing Environment Factors From Signals Generated From Video Images Captured for Biomedical Measurements", U.S. Appl. No. 13/401,207, filed Feb. 21, 2012.
Xu et al., "Monitoring Respiration With a Thermal Imaging System", U.S. Appl. No. 13/103,406, filed May 9, 2011.
Xu et al., "Subcutaneous Vein Pattern Detection Via Multi-Spectral IR Imaging in an Identity Verification System", U.S. Appl. No. 13/087,850, filed Apr. 15, 2011.
Mestha et al., "Deriving Arterial Pulse Transit Time From a Source Video Image", U.S. Appl. No. 13/401,286, filed Feb. 21, 2012.

(Continued)

*Primary Examiner* — Ruth S Smith
(74) *Attorney, Agent, or Firm* — Philip E. Blair; Fleit Gibbons Gutman Bongini & Bianco P.L.

(57) ABSTRACT

What is disclosed is a video system and method that accounts for differences in imaging characteristics of differing video systems used to acquire video of respective regions of interest of a subject being monitored for a desired physiological function. In one embodiment, video is captured using N video imaging devices, where N≥2, of respective regions of interest of a subject being monitored for a desired physiological function (i.e., a respiratory or cardiac function). Each video imaging device is different but has complimentary imaging characteristics. A reliability factor f is determined for each of the devices in a manner more fully disclosed herein. A time-series signal is generated from each of the videos. Each time-series signal is weighted by each respective reliability factor and combined to obtain a composite signal. A physiological signal can be then extracted from the composite signal. The processed physiological signal corresponds to the desired physiological function.

8 Claims, 2 Drawing Sheets

(56) References Cited

PUBLICATIONS

Mestha, et al., "Estimating Cardiac Pulse Recovery From Multi-Channel Source Data Via Constrained Source Separation", U.S. Appl. No. 13/247,683, filed Sep. 28, 2011.

Mestha et al., "Systems and Methods for Non-Contact Heart Rate Sensing", U.S. Appl. No. 13/247,575, filed Sep. 28, 2011.

Mestha et al., "Video-Based Estimation of Heart Rate Variability", U.S. Appl. No. 13/532,057, filed Jun. 25, 2012.

Kyal et al., "Continuous Cardiac Signal Generation From a Video of a Subject Being Monitored for Cardiac Function", U.S. Appl. No. 13/871,766, filed Apr. 26, 2013.

Mestha et al., "Processing a Video for Respiration Rate Estimation", U.S. Appl. No. 13/529,648, filed Jun. 21, 2012.

Mestha et al., "Processing a Video for Vascular Pattern Detection and Cardiac Function Analysis", U.S. Appl. No. 13/483,992, filed May 30, 2012.

Bernal et al., "Processing a Video for Tidal Chest Volume Estimation", U.S. Appl. No. 13/486,637, filed Jun. 1, 2012.

Kyal et al., "Continuous Cardiac Pulse Rate Estimation From Multi-Channel Source Video Data", U.S. Appl. No. 13/528,307, filed Jun. 20, 2012.

Mestha et al., "Filtering Source Video Data Via Independent Component Selection", U.S. Appl. No. 13/281,975, filed Nov. 8, 2011.

Bernal et al., "Respiratory Function Estimation From a 2D Monocular Video", U.S. Appl. No. 13/680,838, filed Nov. 19, 2012.

Wang et al., "Multi-Band Infrared Camera System Optimized for Skin Detection", U.S. Appl. No. 13/416,436, filed Mar. 9, 2012.

Bernal et al., "Minute Ventilation Estimation Based on Depth Maps", U.S. Appl. No. 13/486,682, filed Jun. 1, 2012.

Bernal et al., "Minute Ventilation Estimation Based on Chest Volume", U.S. Appl. No. 13/486,715, filed Jun. 1, 2012.

Mestha et al., "Determining Cardiac Arrhythmia From a Video of a Subject Being Monitored for Cardiac Function", U.S. Appl. No. 13/532,128, filed Jun. 25, 2012.

Tanaka et al., "Processing Source Video for Real-Time Enhancement of a Signal of Interest", U.S. Appl. No. 13/745,283, filed Jan. 18, 2013.

VIDEO ACQUISITION SYSTEM FOR MONITORING A SUBJECT FOR A DESIRED PHYSIOLOGICAL FUNCTION

TECHNICAL FIELD

The present invention is directed to a video acquisition system comprising N video imaging devices, where $N \geq 2$, each capturing video of a respective region of interest of a subject being monitored for a desired physiological function (i.e., a respiratory or cardiac function), and a method of processing time-series signals obtained from those videos to generate a composite signal from which a physiological signal corresponding to the desired physiological function is extracted and analyzed for continuous monitoring.

BACKGROUND

Monitoring of patient cardio-respiratory events is of vital clinical importance in the early detection of potentially fatal conditions. Current technologies that involve contact sensors require that the individual wears such devices constantly. Such a requirement can lead to discomfort, psychological dependence, loss of dignity, and may even cause additional medical issues such as skin infection when sensors have to be worn for an extended period of time. Elderly patients, infants, and those suffering from chronic medical conditions are more likely to suffer from such negative effects of continuous monitoring. The use of an unobtrusive, non-contact, imaging based monitoring of physiological events can go a long way towards alleviating some of these issues.

Previous methods by the authors hereof, and other Xerox researchers, have been directed to systems and methods which employ differing video devices for estimating cardiac and respiratory functions from signals extracted from time-series signals obtained from video of one or more regions of interest of a resting patient. Different imaging devices are utilized because each captures different video signals, each targeted to acquire a different physiological signal, e.g., RGB for heart rate and motion monitoring, thermal for respiration rate and temperature monitoring, and 3D imaging devices for chest volume and minute ventilation estimations. However, each imaging device is also capable of capturing video signals to acquire other physiological signal, for example, RGB for respiration rate, thermal and 3D imaging devices for heart rate estimations. The use of differing video devices to capture video signals that are subsequently fused together to provide a more reliable event monitoring system has its advantages. However, in an integrated imaging system employing a diverse array of different video devices to capture video signals of a subject of interest, Xerox researchers have subsequently determined that differences in the imaging characteristics between an array of video devices need to be taken into account in order to obtain physiological signals for patient event monitoring that are reliable. The teachings hereof are directed to this issue.

Accordingly, what is needed in this art is a video acquisition system comprising N video devices, where $N \geq 2$, with each of the video devices capturing a video of a respective region of interest of a subject being monitored for a desired physiological function for continuous physiological event monitoring of the resting patient.

BRIEF SUMMARY

What is disclosed is an integrated video acquisition system and method that accounts for differences in imaging characteristics of differing video systems used to acquire video of respective regions of interest of a subject being monitored for a desired physiological function. In one embodiment, video is captured using N video imaging devices, where $N \geq 2$, of respective regions of interest of a subject being monitored for a desired physiological function (i.e., a respiratory or cardiac function). Each video imaging device is different but has complimentary imaging characteristics. A reliability factor f is determined for each of the devices. The reliability factor is based upon the physiological function, the region of interest being imaged, the state of the subject, and device signal strength for a set of surrounding environmental conditions. A time-series signal is generated from each of the videos. Each time-series signal is weighted by each device's respective reliability factor and then combined to obtain a composite time-series signal for a desired time segment. A physiological signal is then extracted from the composite time-series signal. The extracted physiological signal corresponds to the desired physiological function. The physiological signal can then be communicated to a display device for continuous physiological event monitoring of the subject in a non-contact, remote sensing environment. The teachings hereof provide for patient monitoring using a variety of different video imaging devices to extract a physiological signal of interest without disturbing the resting patient.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
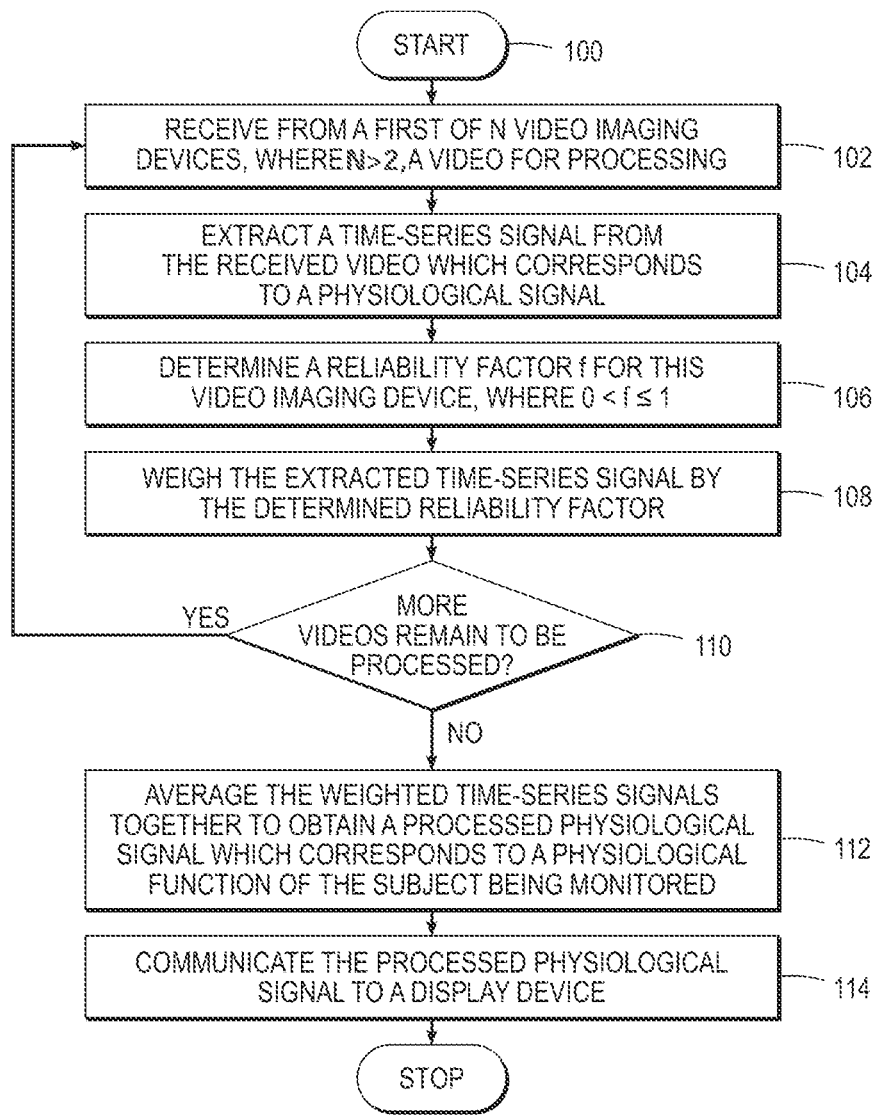
FIG. 1 illustrates a flow diagram of one example embodiment of the present method for monitoring a subject of interest for a physiological function in a non-contact remote sensing environment.

What is disclosed is a video acquisition system and a method to generated a physiological signal which corresponds to a desired physiological function for continuous physiological event monitoring.

NON-LIMITING DEFINITIONS

A "subject of interest" refers to a human having a physiological function. Although the term "human", "person", or "patient" may be used throughout this text, it should be appreciated that the subject may be something other than a human such as, for instance, an animal. Use of "human", "person" or "patient" is not to be viewed as limiting the appended claims strictly to human beings.

A "region of interest" is an area of the subject of interest which, in turn, is processed to determine various aspects of a physiological function which the subject is being monitored for. Automatic region of interest (ROI) selection can be performed based on spatial features or color of the ROI's. For example, for heart rate monitoring using RGB cameras, the ROI's can be exposed skin regions such as faces and hands. Existing face (front/side view) detection/localization methods can be utilized to identify a facial area of the subject in the video frames. For the hands or other areas of exposed skin, the ROI can be identified using color-based localization techniques that rely on identifying body parts by shape. Relative body position can also be used to identify a region of interest. Furthermore, exposed skin areas can be localized through material classification. For example, one video device for skin detection is disclosed in: "Multi-Band Infrared Camera System Optimized For Skin Detection", U.S. Pat. No. 9,171,196, by Wang et al., which is incorporated herein in its entirety by reference. For respiration monitoring using, for instance, thermal cameras, the ROI's are preferably the nostril/mouth region. These ROIs can be identified by temperature differences in the nostril/mouth region of the subject in the acquired video frames. On the other hand, the ROI's for estimating respiration functions using RGB cameras and 3D imaging devices are preferably the anterior or posterior of the thoracic region It should be appreciated that each of the video imaging devices, as defined herein, may be positioned such that each is focused, in whole or in part, on a different region of interest of the same subject. For example, one video imaging device may be focused on the subject's anterior thoracic region, while another video imaging device is focused on the subject's facial region, while yet another video imaging device is focused on an extremity such as the subject's arm or leg, for example. Still another video imaging device may be focused on a region of interest which overlaps one or more other regions of interest being videoed by other video imaging devices, with each video imaging device capturing video of a respective region of interest. It should also be appreciated that all of the video imaging devices may be entirely focused on the same region of interest.

A "video imaging device" is a single-channel or multi-channel video imaging device for acquiring a time-varying sequence of video images. Video imaging devices with differing imaging characteristics include: RGB cameras, 3D video imaging devices, infrared video imaging devices, multi-spectral video systems, hyperspectral video systems, and hybrid devices comprising any combination hereof. Such hybrid devices are capable of operating in differing modes, i.e., a conventional video acquisition mode with high frame rate and high spatial resolution, and a spectral video acquisition mode with high spectral resolution but low spatial resolution. The video imaging devices are different but have complimentary imaging characteristics such as, for instance, different wavelength ranges, frame rates, spatial resolutions, and the like. Each of these differences facilitates a determination of one or more aspects of a desired physiological function for which the subject of interest is being monitored. Such video imaging devices typically have a plurality of outputs from which the captured video can be retrieved or otherwise received on a per-channel basis. These video imaging devices may further comprise one or more processors, memory, and a storage device for executing machine readable program instructions for analyzing video in accordance with the teachings hereof. In various embodiments hereof, the integrated video imaging system comprises a hardware module such as an ASIC with at least one processor for executing machine readable program instructions for analyzing video images on a frame-by-frame basis for physiological signal extraction. Such a module may comprise, in whole or in part, a software application working alone or in conjunction with various hardware resources, which may leverage off the shelf software applications. Such software applications may be executed by one or more processors operating on different hardware platforms or which are emulated in a virtual environment.

A "reliability factor f" for each of the video imaging devices, where $0 < f \leq 1$, is a factor that is based upon, at least in part, the identified physiological function for which the subject of interest is being monitored; the region of interest of the subject that is being imaged; and the signal strength of the video imaging device for a given set of surrounding environmental conditions. Other factors may be added. The reliability factor of each device may be assigned by an operator based upon experience using the various video imaging devices in different environmental conditions. The reliability factor for a given device may be based upon, for example, test results having been conducted using that video imaging device in different environmental conditions. The reliability factor may be based, in whole or in part, on manufacturer specifications and test data. The reliability factor may be updated in real-time, for any given video imaging device, in response to changes in the surrounding environment and/or changes made to a video imaging device.

A "time-series signal" is a signal of interest extracted from a video and which contains meaningful data which relates to the desired physiological function that the subject of interest is being monitored for. A time series signal is formed by averaging pixel values within each ROI for every video frame. A time-series signal comprises signal segments connected together. Some or all of the signal segments comprising a given time-series signal may be weighted by a reliability factor associated with the video imaging device used to acquire the video from which that time-series signal was obtained. Individual signal segments may be weighted over a pre-defined time interval while other signal segments are not weighted. Once the weighting has been applied, signal segments of each of the time-series signals having a same time interval are averaged together to obtain processed signal segments. Each of the processed signal segments are stitched together to obtain a continuous composite time-series signal. Methods for weighting and averaging signal segments are well established in the signal processing arts. The individual signal segments are stitched together using a mid-point or an end-point stitching technique as disclosed in: "Continuous Cardiac Pulse Rate Estimation From Multi-Channel Source Video Data With Mid-Point Stitching", U.S. Pat. No. 9,036,877, by Kyal et al., and "Continuous Cardiac Pulse Rate Estimation From Multi-Channel Source Video Data", U.S. Pat. No. 8,855,384, which are incorporated herein in their entirety by reference. It should be appreciated that the various time-series signals may be generated and processed to obtain a composite time-series signal in real-time from streaming video obtained from each respective video imaging device. Moreover, the physiological signal can be extracted from the composite time-series signal and displayed in real-time on a display device.

"Surrounding environmental conditions" include, for example, lighting, temperature, humidity, altitude, pressure, magnetic field strength, movement of the subject, and the degree by which the region of interest being videoed is occluded by, for example, clothing or other objects. This list is not intended to be exhaustive. An environmental condition may be any condition in the environment in which the present integrated video imaging system and the methods disclosed herein are utilized for their intended purposes, which adversely impacts any aspect of the time-series signal extracted from those video captured by each respective video imaging device.

Physiological Signals

A "physiological signal" refers to a signal extracted from a time-series signal generated from a video of a region of interest.

A "physiological function" refers to a respiratory function or a cardiac function. If the desired physiological function for which the subject is being monitored is a respiratory function then the physiological signal is a respiratory signal. This respiratory signal is analyzed for any of: pulmonary volume, minute ventilation, and respiration rate. The physiological event which the respiratory patient would be monitored for would be the occurrence of Sudden Infant Death Syndrome, Infant Respiratory Distress Syndrome, Respiratory Failure, and/or Pulmonary Disease. If the desired physiological function for which the subject is being monitored is a cardiac function then the physiological signal is a cardiac signal. The cardiac signal is analyzed for any of: heart rate variability, cardiac pulse frequency. In this case, the physiological event for which the cardiac patient would be monitored for would be, for example, the occurrence of any of: Cardiac Arrhythmia, Cardiac Stress, Cardiac Failure, and Heart Disease.

Respiratory Function

A "respiratory function" refers to a function of the lungs. Respiratory functions include: pulmonary volume, minute ventilation, and respiration rate. Regarding pulmonary volumes, TABLE 1 provides average volumes (in liters) for healthy adult human males and females.

TABLE 1

| Volume | Average (in liters) | | Derivation |
|---|---|---|---|
| | In men | In women | |
| Tidal Volume (TV) | 0.5 | 0.5 | |
| Expiratory Reserve Volume (ERV) | 1.0 | 0.7 | |
| Residual Volume (RV) | 1.2 | 1.1 | |
| Inspiratory Reserve Volume (IRV) | 3.3 | 1.9 | |
| Vital Capacity (VC) | 4.6 | 3.1 | IRV + TV + ERV |
| Inspiratory Capacity (IC) | 3.8 | 2.4 | IRV + TV |
| Functional Residual Capacity (FRC) | 2.2 | 1.8 | ERV + RV |
| Total Lung Capacity (TLC) | 6.0 | 4.2 | IRV + TV + ERV + RV |

Expiratory Reserve Volume (ERV) is the maximal volume of air that can be exhaled from the end-expiratory position. Residual Volume (RV) is the volume of air remaining in the lungs after maximal exhalation (residual air remains in the lungs no matter how hard one tries to expel all their air). Inspiratory Reserve Volume (IRV) is the maximal volume of air that can be inhaled at the end-inspiratory level. Vital Capacity (VC) is the maximum amount of air a person can expel from the lungs after maximum inhalation. Inspiratory Capacity (IC) is the volume of air that can be inhaled after normal inspiration. Functional residual capacity (FRC) is the volume in the lungs at the end-expiratory position. Total Lung Capacity (TLC) is the total volume of air in the lungs at maximal inflation.

"Respiration rate" is often measured when a subject is at rest and simply involves counting the number of breaths taken in a minute. A resting adult human takes about 12-20 breaths per minute depending on the overall condition of the cardio-vascular and respiratory systems. Restrictive pulmonary diseases such as pulmonary fibrosis, pneumothorax, Infant Respiratory Distress Syndrome, and the like, decrease lung volume, whereas obstructive pulmonary diseases such as, for instance, asthma, bronchitis, and emphysema, obstruct airflow.

"Chest volume" is the volume of air displaced by inspiration and expiration. Tidal breathing refers to normal breathing as opposed to heavy breathing due to exercise, for example. Thus, tidal chest volume or simply tidal volume (TV) is the volume of air drawn into the lungs during tidal breathing. In a healthy, young adult, tidal chest volume is about 0.5 Liters of air. Since total lung capacity of an average adult human is approximately 6.0 liters of air, the lungs displace a relatively small volume after inspiration and expiration while tidal breathing. Restrictive pulmonary diseases such as pulmonary fibrosis, pneumothorax, and Infant Respiratory Distress Syndrome, decrease lung volume, whereas obstructive pulmonary diseases such asthma, bronchitis, and emphysema, obstruct airflow.

Methods for extracting a respiratory signal from a time-series signal obtained from a video of a region of interest of a subject being monitored in a non-contact, remote sensing environment, are disclosed in the following references which are incorporated herein in their entirety by reference. "Respiratory Function Estimation From A 2D Monocular Video", U.S. patent application Ser. No. 13/680,838, by Bernal et al. "Monitoring Respiration with a Thermal Imaging System", U.S. patent application Ser. No. 13/103,406, by Xu et al. "Processing A Video For Tidal Chest Volume Estimation", U.S. patent application Ser. No. 13/486,637, by Bernal et al. "Minute Ventilation Estimation Based On Depth Maps", U.S. patent application Ser. No. 13/486,682, by Bernal et al. "Minute Ventilation Estimation Based On Chest Volume", U.S. patent application Ser. No. 13/486,715, by Bernal et al. "Processing A Video For Respiration Rate Estimation", U.S. patent application Ser. No. 13/529,648, by Bernal et al. "Respiratory Function Estimation_From A 2D Monocular Video", U.S. patent application Ser. No. 13/680, 838, by Bernal et al.

Cardiac Function

"Cardiac function" refers to the function of the heart and, to a large extent, to the cardio-vascular system. In most species, the heart comprises muscle which repeatedly contracts to pump blood throughout the vascular network. This pumping action generates a pressure wave which generally comprises a forward wave generated by contraction and a reflected wave returning from the periphery. This wave pressing on the walls of the subject's blood vessels as the heart beats correlates to the subject's blood pressure.

"Cardiac pulse frequency" is the frequency of the pulse pressure wave generally given in beats per minute (bpm). An adult human's cardiac pulse frequency is around 72 bpm. Each species has their own normal pulse frequency range. A resting adult human has a cardiac pulse rate of about 72 bpm. The frequency range of the human cardiac pulse is between about 50 bpm to 240 bpm. Each species have their own "normal" heart rate and thus their own cardiac pulse frequency range. Heart rate is proportional to the cardiac output, i.e., the volume of blood the heart can pump expressed in L/min (~5 L/min in an adult human).

"Cardiac output" refers to the volume of blood the heart muscle can pump and is generally expressed in L/min. In an adult human, the cardiac output is approximately 5 L/min. Cardio output is given by: $CO=SV \cdot HR$, where SV is stroke volume, and HR is heart rate in bpm. Stroke volume can be affected by valvular dysfunction and ventricular geometric form. Cardiac output can be determined from an estimated heart rate and knowledge of the stroke volume.

"Heart Rate Variability" (HRV) is where the time interval between heart beats varies. Variation in the beat-to-beat interval is a physiological phenomenon. The SA node receives several different inputs and the instantaneous heart rate or RR interval and its variation are the results of these inputs. The main inputs are the sympathetic nervous system (SNS) and the parasympathetic nervous system (PSNS) and humoral factors. Respiration gives rise to waves in heart rate mediated primarily via the PSNS. Factors that affect the input include the baroreflex, thermoregulation, hormones, sleep-wake cycle, meals, physical activity, and stress. HRV is also known by other terms including: Heart Period Variability, Cycle Length Variability, and RR Variability where R is a point corresponding to the peak of the QRS complex of the ECG wave and RR is the interval between successive R-waves. Spectral analysis of R-waves, i.e., RR interval of a 2 to 5 minute short ECG recording, contains the following components: (1) a very low frequency (VLF) component at a frequency range that is 0.04 Hz; (2) a low frequency (LF) component that is within 0.04 to 0.15 Hz; and (3) a high frequency (HF) component that is within 0.15 to 0.40 Hz. Dominant LF results in a sympathetic response and dominant HF results in a more parasympathetic response. If HF component is dominant, that means parasympathetic influence is significant. When LF is dominant then both sympathetic and parasympathetic influences are dominant. Hence, to perform a HRV assessment, the ratio of LF and HF need to be calculated. There is also an ultra-low frequency component (ULF) which is associated with day and night differences at frequencies <0.003 Hz which are typically observed when the signals have been captured over a period of 18 hours or longer. The physiological explanation of the VLF component is less defined and hence it is not considered in a HRV analysis.

"Cardiac arrhythmia", also known as cardiac dysrhythmia, means an irregular heartbeat caused by a change in the heart's electrical conduction system.

"Atrial fibrillation" (AF or A-fib), is one of the most common cardiac arrhythmias. In AF, the normal regular electrical impulses generated by the sinoatrial node are overwhelmed by disorganized electrical impulses usually originating in the roots of the pulmonary veins, leading to irregular conduction of impulses to the ventricles which generate the heartbeat. In atrial fibrillation, the P waves, which represent depolarization of the atria, are absent, with unorganized electrical activity in their place, and irregular RR intervals due to irregular conduction of impulses to the ventricles. Irregular RR intervals may be difficult to determine if the rate is extremely rapid. AF increases the risk of stroke; the degree of stroke risk can be up to seven times that of the average population, depending on the presence of additional risk factors such as high blood pressure. It may be identified clinically when taking a pulse measurement. The presence of AF can be confirmed with an ECG (or EKG) which demonstrates the absence of P-waves together with an irregular ventricular rate. AF may occur in episodes lasting from minutes to days ("paroxysmal"), or be permanent in nature. A number of medical conditions increase the risk of AF, particularly narrowing of the mitral valve of the heart ("mitral stenosis"). Atrial fibrillation may be treated with medications to either slow the heart rate to a normal range ("rate control") or revert the heart rhythm back to normal ("rhythm control"). The evaluation of atrial fibrillation involves diagnosis, determination of the etiology of the arrhythmia, and classification of the arrhythmia.

Methods for extracting a cardiac signal from a time-series signal obtained from a video of a region of interest of a subject being monitored in a non-contact, remote sensing environment are disclosed in the following references which are incorporated herein in their entirety by reference. "Deriving Arterial Pulse Transit Time From A Source Video Image", U.S. Pat. No. 8,838,209, by Mestha. "Estimating Cardiac Pulse Recovery From Multi-Channel Source Data Via Constrained Source Separation", U.S. Pat. No. 8,617,081, by Mestha et al. "Video-Based Estimation Of Heart Rate Variability", U.S. Pat. No. 8,977,347, by Mestha et al. "Systems And Methods For Non-Contact Heart Rate Sensing", U.S. Pat. No. 9,020,185, by Mestha et al. "Continuous Cardiac Signal Generation From A Video Of A Subject Being Monitored For Cardiac Function", U.S. patent application Ser. No. 13/871,766, by Kyal et al. "Processing A Video For Vascular Pattern Detection And Cardiac Function Analysis", U.S. Pat. No. 8,897,522 by Mestha et al. "Subcutaneous Vein Pattern Detection Via Multi-Spectral IR Imaging In An Identity Verification System", U.S. Pat. No. 8,509,495, by Xu et al. "Method And Systems For Vascular Pattern Localization Using Temporal Features", U.S. Pat. No. 8,977,004, by Liu et al. "Determining Cardiac Arrhythmia From A Video Of A Subject Being Monitored For Cardiac Function", U.S. Pat. No. 8,768,438, by Mestha et al.

Signal Enhancement

Signals obtained by having processed the video may be further processed using the methods disclosed in any of: "Processing Source Video For Real-Time Enhancement Of A Signal Of Interest", U.S. Pat. No. 8,879,867, by Tanaka et al. "Removing Environment Factors From Signals Generated From Video Images Captured For Biomedical Measurements", U.S. Pat. No. 9,185,353, by Mestha et al. "Filtering Source Video Data Via Independent Component Selection", U.S. Pat. No. 8,600,213, by Mestha et al., all of which are incorporated herein in their entirety by reference.

Light Sources

Structured light sources may be used to illuminate a scene wherein the present video system is actively acquiring video of a subject of interest. Structured illumination refers to an illumination source which projects light through a patterned grid or window having known spatial characteristics. Such systems and methods for using structured and unstructured light sources are disclosed in: "Contemporaneously Reconstructing Images Captured Of A Scene Illuminated With Unstructured And Structured Illumination Sources", U.S. Pat. No. 9,141,868, by Xu et al., and "Enabling Hybrid Video Capture Of A Scene Illuminated With Unstructured And Structured Illumination Sources", U.S. Pat. No. 9,155,475, by Xu et al., which are incorporated herein in their entirety by reference. Light sources can also be in different wavelength bands, with broad or narrow-band illumination without any structure such that they do not interfere with each imaging device.

Flow Diagram

Reference is now being made to the flow diagram of FIG. 1 which illustrates a flow diagram of one example embodiment of the present method for monitoring a subject of interest for a physiological function in a non-contact remote sensing environment. Flow processing begins at 100 and immediately proceeds to step 102.

At step 102, receive, from a first of N video imaging devices, where $N \geq 2$, a video of a region of interest for processing. The video has been acquired of a subject of interest being monitored for a physiological function.

A step 104, extract a time-series signal from the received video.

At step 106, determine a reliability factor f for this video imaging device, where $0 < f \leq 1$.

At step 108, weight the extracted time-series signals by this video imaging device's respective reliability factor.

At step 110, a determination is made whether to receive another video for processing. If so then processing continues with respect to step 102 wherein a next video is received which has been acquired using a next video imaging device. A reliability factor is then determined for this next device and a time-series signal is extracted and weighted by this next device's respective reliability factor. It should be understood that all the time-series signals are preferably sampled at the same frequency otherwise they will have to be re-sampled at the same frequency before they can be combined. Flow processing repeats until, at step 110, there are no more videos to be processed.

At step 112, average the weighted signals together to obtain a processed physiological signal. The processed physiological signal corresponds to the desired physiological function for which the subject of interest is being monitored. In another embodiment, the physiological parameter is estimated from each of the video imaging devices that are capable of producing such data and then that data is combined to create a composite physiological parameter with respect to time. This then becomes the physiological signal. This may be of interest to us because it can improve reliability.

At step 114, communicate the processed physiological signal to a display device. The processed physiological signal may be communicated to a storage device for storage and subsequent retrieval or communicated to a remote device over a network. In this embodiment, further processing ends.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of a Video Processing System

Figure 2:
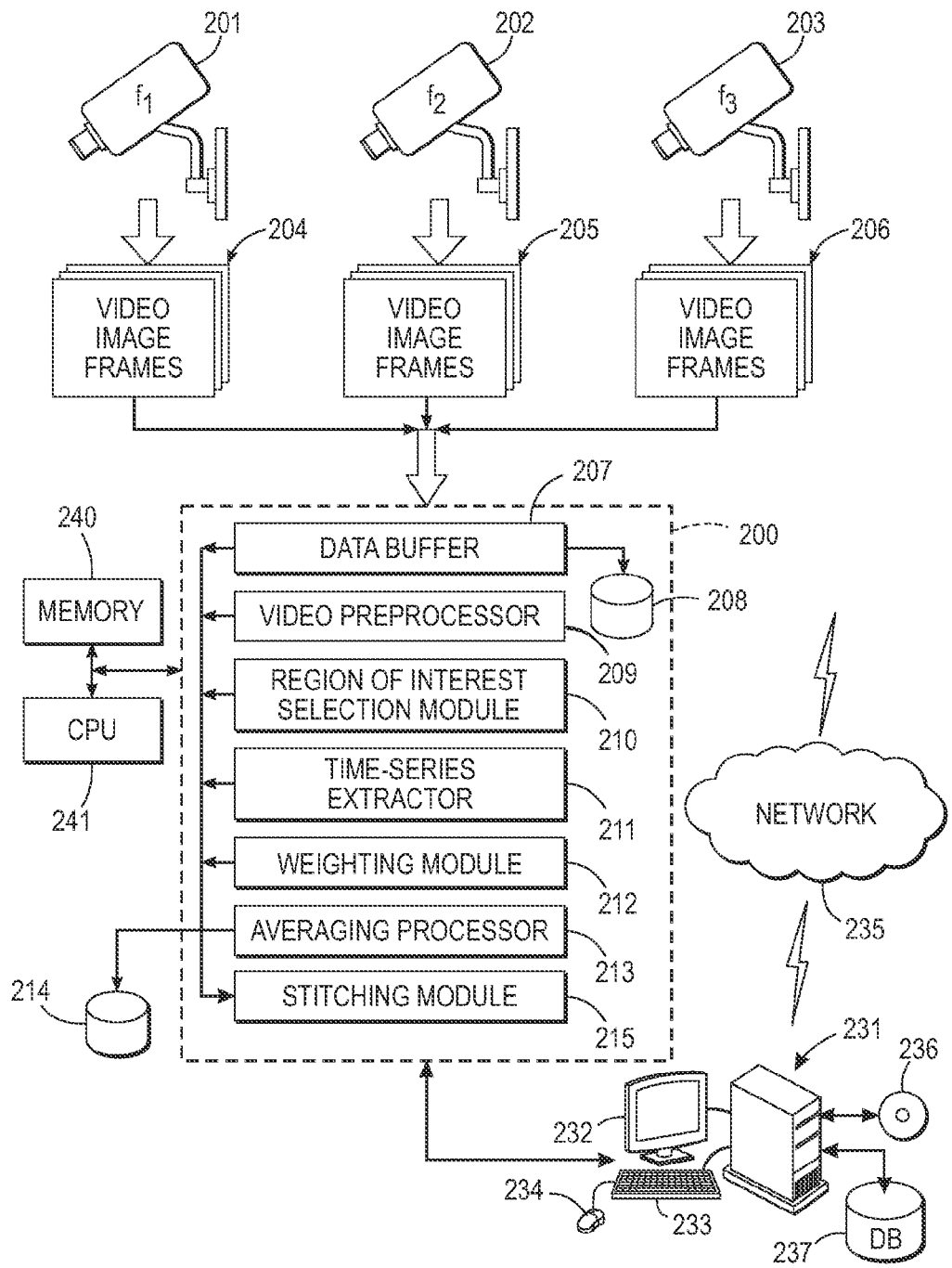
FIG. 2 is a block diagram of one example video processing system for processing received video in accordance with the embodiment shown and described with respect to the flow diagram of FIG. 1.

Reference is now being made to FIG. 2 which is a block diagram of one example video processing system for processing video in accordance with the embodiment shown and described with respect to the flow diagram of FIG. 1.

In this embodiment, three different video imaging devices, at 201, 202 and 203, respectively, are used to acquire a time varying sequence of video images, at 204, 205 and 206, respectively. Each of the video imaging devices has different but have complimentary imaging characteristics which facilitate a determination of the subject's physiological function. Video image device 201 is, for example, a RGB video camera. Video image device 202 is, for example, an IR video camera, and video imaging device 203 is, for example, a multi-spectral video camera. Each of the video imaging devices also has a reliability factor f which, in this embodiment, had been assigned by an operator based upon experience using these video imaging devices in different environmental conditions. The assigned reliability factors are given as $f_1$, $f_2$, $f_3$, respectively. The video image frames acquired by each respective video imaging device and the respective reliability factors are received by the image processing system into Data Buffer 207 which buffers the received data to Storage Device 208 which may comprise any of: a hard drive, RAM, ROM, or a device with a removable media such as a DVD or CDROM drive. Video Pre-Processor Module 209 is shown for those systems where it is desirable to pre-process the received video in advance of processing in accordance with the methods disclosed herein. The received video may be pre-processed, for example, to enhance contrast utilizing known contrast enhancement techniques such as histogram equalization or contrast adjustment. Image frames can be skew and rotation corrected if needed. Gaps detected between video image frames in each of the x and y directions can be corrected as desired. Various images can be boundary corrected and cropped and frame registration performed. Images can be pre-processed for relative shift due to the location of each filter band within the filter and camera-to-object distance can also be corrected, if needed. Intensity values associated with pixels of images can be re-scaled based on a sensor response of each wavelength band of the video systems.

Region of Interest Selection Module 210 facilitates or otherwise effectuates a selection of one or more regions of interest in the video. In one embodiment, the pre-processed video image frames are communicated to workstation 231 and displayed, for example, on a split-screen of graphical display 232 such that a region of interest of a subject being monitored for a physiological condition can be visually identified and selected. For example, upon an operator of workstation 231 may select an area of interest using keyboard 233 and mouse 234 to make a selection by, for instance, placing a rubber-band box around one or more areas of interest encompassing in the received video. In one embodiment, the user-selected areas of interest are provided from the workstation back to Module 210. In another embodiment, the areas of interest in the received video are automatically identified by Module 210 using, for example, a pixel classification technique, facial recognition software, and/or object identification and tracking methods.

Time-Series Signal Extractor 211 processes each of the received videos and extracts therefrom a time-series signal associated with the identified region of interest. The extracted time-series signals are broken into segments using, for example, a sliding window. The signal segments are then provided to Weighting Module 212 wherein a weighting, as defined by each video imaging device's respective reliability factor, is applied to some or all of the individual signal segments comprising each respective time-series signal. Averaging Processor 213 receives these time-series signals and proceeds to average together signal segments which have a same time interval to generate a processed signal segments. The processed signal segments are stored to Storage Device 214, which may be the same as Storage Device 208. The processed signal segments are retrieved by Stitching Module 215 which proceeds to stitch all the processed signal segments together to form a continuous processed physiological signal that corresponds to the desired physiological function which the subject is being monitored for. The processed physiological signal may also be displayed on the display 232 of the workstation 231. The workstation communicates the processed physiological signals to one or more remote devices over network 235 for further processing or storage. The processed physiological signals may also be communicated to storage devices 236 and 237.

Memory 240 and CPU 241 are shown in communication with the video processing system 200 to provide processing support to any of the modules and processing units of the video processing system. Such processing may take the form of facilitating a communication between the various modules and with the workstation. Memory 240 may further store/retrieve data, variables, records, parameters, functions, machine readable/executable program instructions required to facilitate a performance of any of the intended functions of the modules and processing units. It should be understood that any of the modules and processing units of the embodiment of FIG. 2 can be placed in communication with workstation 231 via pathways not shown. Each of the modules of video processing system 200 may be placed in communication with one or more devices over network 235. It should be appreciated that some or all of the functionality for any of the modules of system 200 may be performed, in whole or in part, by components internal to workstation 231 or by a special purpose computer system.

Various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network.

One or more aspects of the systems and method described herein are intended to be incorporated in an article of manufacture. The article of manufacture may be shipped, sold, leased, or otherwise provided separately either alone or as part of an add-on, update, upgrade, or product suite. Various of the above-disclosed features and functions, or alternatives thereof, may be combined into other systems or applications. Presently unforeseen or unanticipated alternatives, modifications, variations, or improvements may become apparent and/or subsequently made by those skilled in the art which are also intended to be encompassed by the following claims. It will be appreciated that the above-disclosed and other features and functions, or alternatives thereof, may be desirably combined into many other different systems or applications. Changes to the above-described embodiments may be made without departing from the spirit and scope of the invention.

The teachings of any printed publications including patents and patent applications, are each separately hereby incorporated by reference in their entirety.

What is claimed is:

1. A system for monitoring a subject of interest for a desired physiological function, the system comprising:
    N video imaging devices, where N≥2, each of said video imaging devices concurrently capturing a video of a respective region of interest of a subject being monitored for a desired physiological function; and
    a processor in communication with a memory, said processor executing machine readable program instructions for performing the steps of:
        receiving a time-series signal generated from videos captured by each of said N video imaging devices all of said time-series signals having been sampled at a same frequency, said videos having been captured concurrently by N video imaging devices, where N≥2 and each of said video devices being a different type of video device relative to each other that capture complementary imaging characteristics;
        receiving a reliability factor f for each of said video imaging devices, where 0<f≤1, wherein each of said reliability factors is assigned by an operator based at least in part upon said desire physiological function for which said subject is being monitored, a region of interest of said subject being imaged, and a signal strength of said video imaging device for a given set of surrounding environmental conditions;
        weighting said time-series signals by each video imaging device's respective assigned reliability factor;
        combining said time-series signals to obtain a composite time-series signal; and
        processing said composite time-series signal to obtain a processed physiological signal that corresponds to said desired physiological function.

2. The system of claim 1, wherein one of said N video imaging devices comprise any of: a RGB video device, a 3D video imaging device, an infrared video imaging device, a multi-spectral video imaging device, and a hyperspectral video imaging device.

3. The system of claim 1, wherein said desired physiological function is a cardiac function, and said processed physiological signal is a cardiac signal, further comprising said processor analyzing said cardiac signal to determine any of: cardiac output, heart rate variability, and cardiac pulse frequency.

4. The system of claim 1, wherein said desired physiological function is a cardiac function, and said processed physiological signal is a cardiac signal, further comprising said processor using said cardiac signal to determine an occurrence of any of: Cardiac Arrhythmia, Cardiac Stress, Cardiac Failure, and Heart Disease.

5. The system of claim 1, wherein said desired physiological function is a respiratory function and said processed physiological signal is a respiratory signal, further comprising said processor analyzing said respiratory signal to determine any of: pulmonary volume, minute ventilation, and respiration rate.

6. The system of claim 1, wherein said desired physiological function is a respiratory function and said processed physiological signal is a respiratory signal, further comprising said processor using said respiratory signal to determine an occurrence of any of: Sudden Infant Death Syndrome, Respiratory Distress, Respiratory Failure, and Pulmonary Disease.

7. The system of claim 1, wherein said videos are live streaming videos and said processed physiological signal is generated by said processor in real-time.

8. The system of claim 1, further comprising said processor communicating said processed physiological signal to any of: a storage device, a display device, and a remote device over a network.

* * * * *